(12) United States Patent
Lord

(10) Patent No.: US 10,398,180 B2
(45) Date of Patent: *Sep. 3, 2019

(54) ELECTRONIC VAPOR PROVISION DEVICE

(71) Applicant: Nicoventures Holdings Limited, London (GB)

(72) Inventor: Christopher Lord, London (GB)

(73) Assignee: Nicoventures Holdings Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/886,096

(22) Filed: Feb. 1, 2018

(65) Prior Publication Data

US 2018/0153223 A1 Jun. 7, 2018

Related U.S. Application Data

(62) Division of application No. 14/401,508, filed as application No. PCT/EP2013/059936 on May 14, 2013, now Pat. No. 9,918,497.

(30) Foreign Application Priority Data

May 14, 2012 (GB) .................................. 1208349.9

(51) Int. Cl.
*A24F 47/00* (2006.01)
*H02J 7/34* (2006.01)
(Continued)

(52) U.S. Cl.
CPC .............. *A24F 47/008* (2013.01); *A61M 1/34* (2013.01); *H02J 7/345* (2013.01); *H05B 1/0244* (2013.01); *A61M 2205/50* (2013.01)

(58) Field of Classification Search
CPC combination set(s) only.
See application file for complete search history.

(56) References Cited

U.S. PATENT DOCUMENTS 2,057,353 A 10/1936 Whittemore, Jr.
4,947,875 A 8/1990 Brooks
(Continued)

FOREIGN PATENT DOCUMENTS

CA 2641869 5/2010
CN 1280661 A 1/2001
(Continued)

OTHER PUBLICATIONS

Microcontroller; https://www.techopedia.com/definition/3641/microcontroller (Year: 2018).*
(Continued)

*Primary Examiner* — Eric Yaary
(74) *Attorney, Agent, or Firm* — Patterson Thuente Pedersen, P.A.

(57) ABSTRACT

An electronic vapor provision device comprising a battery assembly and a vaporizer, wherein the battery assembly comprises a power cell and a computer, the vaporizer is releasably connectable to the battery assembly and the computer comprises a computer processor and a memory, wherein the computer is configured to detect whether the vaporizer is connected to the battery assembly without use of the electronic vapor provision device by a user, and to substantially remain in a sleep mode until the vaporizer is connected to the battery assembly.

13 Claims, 4 Drawing Sheets

(51) Int. Cl.
  *A61M 1/34* (2006.01)
  *H05B 1/02* (2006.01)

(56) References Cited

U.S. PATENT DOCUMENTS

| | | | |
|---|---|---|---|
| 5,095,921 A | 3/1992 | Losee | |
| 5,144,962 A | 9/1992 | Counts et al. | |
| 5,372,148 A * | 12/1994 | McCafferty | A24F 47/008 |
| | | | 128/202.21 |
| 5,661,470 A | 8/1997 | Karr | |
| 5,894,841 A | 4/1999 | Voges | |
| 6,183,425 B1 | 2/2001 | Whalen | |
| 6,196,218 B1 | 3/2001 | Voges | |
| 6,958,691 B1 | 10/2005 | Anderson et al. | |
| 7,726,320 B2 | 6/2010 | Robinson | |
| 7,726,329 B2 | 6/2010 | Robinson | |
| 7,852,041 B2 | 12/2010 | Lam | |
| 8,550,069 B2 | 10/2013 | Alelov | |
| 8,674,656 B2 | 3/2014 | Iio | |
| 8,997,753 B2 | 4/2015 | Li | |
| 9,032,968 B2 | 5/2015 | Glasberg | |
| 9,289,014 B2 | 3/2016 | Tucker | |
| 9,451,791 B2 | 9/2016 | Sears | |
| 9,462,832 B2 | 10/2016 | Lord | |
| 9,497,999 B2 | 11/2016 | Lord | |
| 9,597,466 B2 | 3/2017 | Henry | |
| 9,905,175 B2 | 2/2018 | Lee et al. | |
| 2003/0033055 A1 | 2/2003 | McRae et al. | |
| 2003/0123328 A1 | 7/2003 | Guanter | |
| 2003/0179003 A1 | 9/2003 | Toda | |
| 2003/0226837 A1 | 12/2003 | Blake | |
| 2004/0149297 A1 | 8/2004 | Sharpe | |
| 2005/0016550 A1 | 1/2005 | Katase | |
| 2005/0031148 A1 * | 2/2005 | McNary | H04R 1/2811 |
| | | | 381/334 |
| 2005/0045193 A1 | 3/2005 | Yang | |
| 2005/0058441 A1 | 3/2005 | Kameyama | |
| 2005/0067503 A1 | 3/2005 | Katase | |
| 2005/0143866 A1 | 6/2005 | McRae | |
| 2005/0166076 A1 | 7/2005 | Truong | |
| 2005/0268911 A1 | 12/2005 | Cross | |
| 2006/0047368 A1 | 3/2006 | Maharajh | |
| 2007/0045288 A1 | 3/2007 | Nelson | |
| 2007/0267031 A1 | 11/2007 | Hon | |
| 2008/0257367 A1 | 10/2008 | Paterno | |
| 2009/0058578 A1 | 3/2009 | Huang | |
| 2009/0072783 A1 | 3/2009 | Gaspar | |
| 2009/0095311 A1 | 4/2009 | Han | |
| 2009/0115745 A1 | 5/2009 | Chuang | |
| 2009/0230117 A1 | 9/2009 | Fernadno | |
| 2009/0283103 A1 | 11/2009 | Nielsen | |
| 2010/0011234 A1 * | 1/2010 | Malik | G06F 1/26 |
| | | | 713/323 |
| 2010/0052660 A1 | 3/2010 | Wang | |
| 2010/0109889 A1 | 5/2010 | Deng | |
| 2010/0242974 A1 | 9/2010 | Guocheng | |
| 2010/0289499 A1 * | 11/2010 | Bremmer | B60K 6/46 |
| | | | 324/503 |
| 2011/0036346 A1 | 2/2011 | Cohen | |
| 2011/0113368 A1 | 5/2011 | Carvajal | |
| 2011/0210746 A1 | 9/2011 | Yugou | |
| 2011/0226236 A1 * | 9/2011 | Buchberger | A61M 11/041 |
| | | | 128/200.23 |
| 2011/0226266 A1 | 9/2011 | Tao | |
| 2011/0265806 A1 * | 11/2011 | Alarcon | A24F 47/00 |
| | | | 131/273 |
| 2011/0304282 A1 | 12/2011 | Li et al. | |
| 2012/0048266 A1 | 3/2012 | Alelov | |
| 2012/0170177 A1 | 7/2012 | Pertuit | |
| 2012/0227753 A1 | 9/2012 | Newton | |
| 2012/0318882 A1 | 12/2012 | Abehasera | |
| 2013/0037041 A1 | 2/2013 | Worm et al. | |
| 2013/0042865 A1 | 2/2013 | Monsees et al. | |
| 2013/0104916 A1 | 5/2013 | Bellinger et al. | |
| 2013/0169230 A1 | 7/2013 | Li et al. | |

| | | |
|---|---|---|
| 2013/0192615 A1 | 8/2013 | Tucker |
| 2013/0207455 A1 | 8/2013 | Doljack |
| 2013/0228191 A1 | 9/2013 | Newton |
| 2013/0255702 A1 | 10/2013 | Griffith |
| 2013/0284192 A1 | 10/2013 | Peleg |
| 2013/0340775 A1 | 12/2013 | Juster |
| 2014/0053858 A1 | 2/2014 | Liu |
| 2014/0123990 A1 | 5/2014 | Timmermans |
| 2015/0047661 A1 | 2/2015 | Blackley |
| 2015/0114408 A1 | 4/2015 | Lord |
| 2015/0128965 A1 | 5/2015 | Lord |
| 2015/0128966 A1 | 5/2015 | Lord |
| 2015/0128972 A1 | 5/2015 | Verleur |
| 2015/0136153 A1 | 5/2015 | Lord |
| 2015/0237917 A1 | 8/2015 | Lord |
| 2015/0245660 A1 | 9/2015 | Lord |
| 2015/0257448 A1 | 9/2015 | Lord |
| 2015/0336689 A1 | 11/2015 | Brown |
| 2016/0049804 A1 | 2/2016 | Lee |
| 2016/0206000 A1 | 7/2016 | Lord et al. |
| 2016/0226286 A1 | 8/2016 | Xiang |
| 2016/0242466 A1 | 8/2016 | Lord |
| 2017/0035114 A1 | 2/2017 | Lord |

FOREIGN PATENT DOCUMENTS

| | | |
|---|---|---|
| CN | 1284493 | 11/2006 |
| CN | 201029436 Y | 3/2008 |
| CN | 201238610 Y | 5/2009 |
| CN | 101518361 A | 9/2009 |
| CN | 101557728 A | 10/2009 |
| CN | 100566769 C | 12/2009 |
| CN | 201379072 Y | 1/2010 |
| CN | 201393548 Y | 2/2010 |
| CN | 101969800 | 2/2011 |
| CN | 101977522 | 2/2011 |
| CN | 201821914 U | 5/2011 |
| CN | 201830899 U | 5/2011 |
| CN | 102264251 | 11/2011 |
| CN | 102298435 A | 12/2011 |
| CN | 202474905 U | 10/2012 |
| CN | 102934843 A | 2/2013 |
| CN | 102970885 A | 3/2013 |
| CN | 202890466 U | 4/2013 |
| CN | 203070141 U | 7/2013 |
| CN | 103237468 A | 8/2013 |
| CN | 203504217 U | 3/2014 |
| DE | 202005018998 U1 | 2/2006 |
| EP | 1712178 A2 | 10/2006 |
| EP | 2 100 525 | 9/2009 |
| EP | 2 110 034 A1 | 10/2009 |
| EP | 2 201 850 | 6/2010 |
| EP | 2 383 861 A2 | 11/2011 |
| EP | 2 404 515 A1 | 1/2012 |
| EP | 2460423 A1 | 6/2012 |
| GB | 2468932 | 9/2010 |
| GB | 2502053 A | 11/2013 |
| GB | 2502055 A | 11/2013 |
| GB | 2502162 A | 11/2013 |
| GB | 2502163 A | 11/2013 |
| GB | 2502164 A | 11/2013 |
| JP | 05-307439 | 11/1993 |
| JP | 10-320082 A | 5/1997 |
| JP | 2006-018057 | 1/2006 |
| JP | 2006-338178 | 12/2006 |
| JP | 2011-087569 A | 5/2009 |
| JP | 2012090427 | 5/2012 |
| KR | 20110002227 U | 3/2011 |
| RU | 2336001 C2 | 10/2008 |
| RU | 2336002 C2 | 10/2008 |
| RU | 2360583 C1 | 11/2009 |
| RU | 94815 U1 | 6/2010 |
| WO | WO9118860 A1 | 12/1991 |
| WO | WO 9418860 A1 | 9/1994 |
| WO | WO9501137 A1 | 1/1995 |
| WO | WO 98/17130 | 4/1998 |
| WO | WO98017131 A1 | 4/1998 |
| WO | WO 2000050111 | 8/2000 |
| WO | WO0064517 A1 | 11/2000 |

(56) References Cited

FOREIGN PATENT DOCUMENTS

| | | |
|---|---|---|
| WO | WO2013098397 | 12/2001 |
| WO | WO2012/109371 | 8/2002 |
| WO | WO2013060874 A2 | 5/2003 |
| WO | WO 2004/080216 A1 | 9/2004 |
| WO | WO 2004/095955 A1 | 11/2004 |
| WO | WO 2007074430 A1 | 7/2007 |
| WO | WO 2009032064 A2 | 3/2009 |
| WO | WO2004041007 | 8/2009 |
| WO | WO 2009118085 | 10/2009 |
| WO | WO2010040015 | 4/2010 |
| WO | WO 2010091593 | 8/2010 |
| WO | WO 2010118644 | 10/2010 |
| WO | WO 2012065754 A2 | 11/2010 |
| WO | WO2010145805 A1 | 12/2010 |
| WO | WO2013060781 | 10/2011 |
| WO | WO 2011137453 A2 | 11/2011 |
| WO | WO 2011147699 | 12/2011 |
| WO | WO 2012/048266 | 4/2012 |
| WO | WO 2013025921 A1 | 2/2013 |
| WO | WO 2013060784 A2 | 5/2013 |
| WO | WO 2013126770 A1 | 8/2013 |
| WO | WO2013138384 A2 | 9/2013 |
| WO | WO2013148810 A1 | 10/2013 |
| WO | WO2014037794 A2 | 3/2014 |
| WO | WO2014054035 A1 | 4/2014 |

OTHER PUBLICATIONS

Japanese Office Action, Application No. 2017-153826, dated Jun. 19, 2018, 3 pages (6 pages with translation).
Korean Office Action, Application No. 20157010072, dated Apr. 27, 2018, 10 pages (19 pages with translation).
Russian Search Report, Application No. 2016147728/12, dated Mar. 27, 2018, 3 pages (6 pages with translation).
Russian Decision to Grant, Application No. 2015114351/12, dated Aug. 24, 2016, 12 pages.
Chinese Office Action, Application No. 201480055728.2, dated Nov. 17, 2017, 8 pages (20 pages with translation).
Japanese Search Report, Application No. 2016-520611, dated Mar. 28, 2017, 18 pages (46 pages with translation).
Japanese Office Action, Application No. 2016-520611, dated May 9, 2017, 6 pages (11 pages with translation).
Korean Office Action, Application No. 10-2016-7009422, dated Jul. 26, 2017, 8 pages (17 pages with translation).
Australian Third Extended Report, Application No. 2014333571, dated May 23, 2017, 4 pages.
Australian First Examination Report, Application No. 2013261801, dated Jul. 10, 2015, 2 pages.
Australian First Extended Report, Application No. 2013331849, dated Dec. 1, 2015, 3 pages.
Australian First Extended Report, Application No. 2014333571, dated Nov. 25, 2016, 4 pages.
Australian Second Examination Report, Application No. 2013261801, dated Jun. 23, 2016, 3 pages.
Australian Second Extended Report, Application No. 2013331849, dated May 2, 2016, 3 pages.
Australian Second Extended Report, Application No. 2014333571, dated Jan. 23, 2017, 4 pages.
European Extended Search Report, Application No. 17192572.0, dated Mar. 14, 2018, 8 pages.
Canadian Office Action, Application No. 2,872,764, dated Aug. 31, 2016, 6 pages.
Canadian Office Action, Application No. 2,872,764, dated Oct. 5, 2015, 6 pages.
Canadian Office Action, Application No. 2,886,922, dated Mar. 4, 2016, 3 pages.
Canadian Office Action, Application No. 2,922,280, dated Jan. 20, 2017, 4 pages.
Chinese Office Action, Application No. 201380025370.4, dated Oct. 11, 2016, 3 pages (8 pages with translation).
Chinese Office Action, Application No. 201380054442.8, dated Jun. 28, 2017, 8 pages.
Corrected IPRP, International Application No. PCT/EP2013/071070, dated Jun. 19, 2015, 13 pages.
EP Office Action, Application No. 13779773, dated Aug. 7, 2017, 2 pages.
European Extended Report, Application No. 13779773.4, dated Jun. 20, 2016, 2 pages.
Japanese Decision to Grant, Application No. 2015-537196, dated Jul. 6, 2017, 3 pages (6 pages with translation).
Japanese Office Action, Application No. 2015-537196, dated Mar. 22, 2016, 3 Pages (7 pages with translation).
Japanese Office Action, Application No. 2015-537196, dated Nov. 22, 2016, 4 pages (9 pages with translation).
Korean Office Action, Application No. 10-2014-7035201, dated Sep. 23, 2016, 6 pages.
New Zealand Extended Report, Application No. 71778, dated Aug. 15, 2016, 3 pages.
New Zealand First Examination Report, Application No. 717778, dated May 2, 2016, 4 pages.
New Zealand Extended Report, Application No. 717778, dated Nov. 16, 2016, 1 page.
Chinese Office Action, Chinese Patent Application No. 201380025843.7, dated May 4, 2016, 9 pages.
Application and File History for U.S. Appl. No. 14/401,508, filed Nov. 14, 2014, inventor Lord.
PCT International Search Report and Written Opinion of the International Searching Authority for PCT/GB2014/052625, dated Feb. 6, 2015, 16 pages.
PCT International Preliminary Report on Patentability for PCT/GB2014/052625, dated Dec. 3, 2015, 22 pages.
International Preliminary Report on Patentability dated Apr. 23, 2014 for PCT/EP2013/059936 filed May 14, 2013.
Vaishali et al., Random and Periodic Sleep Schedules for Target Detection in Sensor Networks, Journal of Computer Science and Technology, May 2008, 23(3) pp. 343-354.
Load Detecting Power Supply (National Semiconductor RD-166 Production Applications Design Center) Dec. 2008.
International Search Report and Written Opinion, dated Sep. 18, 2013, for PCT/EP2013/059946, filed May 14, 2013.
Application and File History for U.S. Appl. No. 14/401,501, filed Nov. 14, 2014, inventor Lord.
Application and File History for U.S. Appl. No. 14/912,598, filed Feb. 17, 2016, inventor: Lord.
Chinese Office Action, Application No. 201380025459.0, dated Feb. 14, 2016, 7 pages (19 pages with translation).
Russian Search Report, Application No. 2014 150 420, dated Aug. 8, 2016, 3 pages.
Japanese Office Action, Application No. 2016537385, dated Mar. 14, 2017, 6 pages.
Japanese Decision to Grant, Application No. 2016537385, dated Sep. 27, 2017.
Korean Office Action, Application No. 20147035025, 2 pages, dated May 26, 2017.
Russian Office Action, Application No. 2014150419/12(080853), dated Jun. 24, 2016, 10 pages.
Great Britain Search Report, Application No. GB1208349.9, dated Sep. 14, 2012, 1 page.
Japanese Search Report, Application No. 2016-537385, dated Feb. 22, 2017, 43 pages (56 pages with translation).
Chinese Search Report/Office Action, Application No. 201480047679.8, dated Jul. 14, 2017, 5 pages.
Chinese Office Action, Application No. 201380025459.0, dated Oct. 27, 2016, 12 pages.
PCT International Preliminary Report on Patentability for PCT/GB2014/053027, dated Dec. 10, 2015, 19 pages.
International Preliminary Report on Patentability, for PCT/EP2013/059954, dated Jul. 10, 2014.
Written Opinion, for PCT/EP2013/059954, dated Apr. 16, 2014, 5 pages.
International Search Report, for PCT/EP2013/059954, dated Sep. 25, 2013, 8 pages.

(56) References Cited

OTHER PUBLICATIONS

Korean Office Action, Application No. KR 10-2014-7035205, dated Aug. 11, 2016, 6 pages.
Chinese Office Action, Application No. CN 201380025370.4, dated Mar. 21, 2016, 9 pages.
International Search Report, for PCT/EP2013/071070, dated Apr. 2, 2014, 6 pages.
International Preliminary Report on Patentability, for PCT/EP2013/071070, dated Nov. 21, 2014, 5 pages.
Search Report and Written Opinion, for PCT/GB2014/053027, dated Apr. 22, 2015, 13 pages.

* cited by examiner

ELECTRONIC VAPOR PROVISION DEVICE

RELATED APPLICATIONS

This application is a division of application Ser. No. 14/401,508 filed Nov. 14, 2014, which in turn is a National Phase entry of PCT Application No. PCT/EP2013/059936, filed May 14, 2013, which in turn claims priority to and benefit of British Patent Application No. GB1208349.9, filed May 14, 2012, each of which is hereby fully incorporated herein by reference.

FIELD

The specification relates to electronic vapor provision devices. More particularly, but not exclusively, the specification concerns electronic vapor provision devices such as electronic cigarettes.

BACKGROUND

Electronic vapor provision devices are typically cigarette-sized and function by allowing a user to inhale a nicotine vapor from a liquid store by applying a suction force to a mouthpiece. Some electronic vapor provision devices have an airflow sensor that activates when a user applies the suction force and causes a heater coil to heat up and vaporize the liquid. Electronic vapor provision devices include electronic cigarettes.

SUMMARY

In an embodiment there is provided an electronic vapor provision device comprising a battery assembly and a vaporizer, where the battery assembly comprises a power cell and a computer, the vaporizer is releasably connectable to the battery assembly and the computer comprises a computer processor and a memory; wherein the computer is configured to detect whether the vaporizer is connected to the battery assembly without use of the electronic vapor provision device by a user; and to substantially remain in a sleep mode until the vaporizer is connected to the battery assembly.

This has the advantage that the technical interaction between the computer and the vapor provision device enables the computer to distinguish between a vaporizer connected state and a vaporizer non connected state. The device can then be configured accordingly.

The sleep mode may be a low power mode.

By remaining in a low power sleep mode the device remains active yet consumes very little power. This has the advantage that the device can be charged, for instance during manufacture, and remain in a sleep mode until purchased and used by a consumer. The device will therefore have sufficient power remaining to be used without first charging the device. This also provides an efficient use of power and minimizes energy wastage. The device has a further advantage that it can remain in a low power mode without the additional user of a switch to deactivate and activate.

The computer can be configured to enter a connected mode when the vaporizer is connected to the battery assembly.

The electronic vapor provision device may use less power in sleep mode than in connected mode.

Advantageously, once the vaporizer has been connected, the connected mode is a higher power state to enable a more rapid activation once the device is activated by a user.

The computer may be configured to wake from sleep mode after a predetermined sleep time to determine whether the vaporizer is connected to the battery assembly. Moreover, the computer may be configured to re-enter sleep mode if a vaporizer is not connected to the battery assembly.

The computer can be configured such that the time between entering consecutive sleep modes when the vaporizer is not connected is less that the sleep time.

The device may enter a low power sleep mode, then wake to test connection before quickly re-entering a low power sleep mode. This maintains a low power usage while in a sleep mode and between sleep modes.

The sleep time may have a value between 0.5 and 5 seconds.

The battery assembly may further comprises a capacitor; wherein the computer is configured to first charge the capacitor and then detect whether a vaporizer is connected to the battery assembly by measuring whether the capacitor is discharged. Furthermore, the computer may be configured to enter a sleep mode when the capacitor is not substantially fully discharged. Moreover, the computer may be configured to enter a connected mode when the capacitor is substantially fully discharged. In other words, the computer may be configured to determine that the vaporizer is not connected to the battery assembly when the capacitor is not substantially fully discharged. Furthermore, the computer may be configured to determine that the vaporizer is connected to the battery assembly when the capacitor is substantially fully discharged.

The battery assembly can further comprise first and second battery assembly connection terminals, and the vaporizer can comprise first and second vaporizer connection terminals, such that the vaporizer is connected to the battery assembly when the first battery assembly connection terminal is connected to the first vaporizer connection terminal and the second battery assembly connection terminal is connected to the second vaporizer connection terminal; wherein the capacitor is connected in parallel with the first and second battery assembly connection terminals.

The battery assembly may further comprise a resistor in series with the capacitor; wherein the capacitor and resistor are in parallel with the first and second battery assembly connection terminals.

The computer may be configured to send out a pulse and the capacitor may be charged for a period of time equal to the width of the pulse.

The electronic vapor provision device may further comprise a transistor; wherein the pulse is sent to the transistor and the transistor opens the current from the power cell to the capacitor for a period of time equal to the width of the pulse.

In another embodiment there is provided an electronic vapor provision device comprising a battery assembly and a vaporizer, wherein the battery assembly comprises a power cell and a computer; the vaporizer is releasably-attachable to the battery assembly; the computer comprises a computer processor, a memory and an input-output means; and the computer is configured in use to detect whether the vaporizer is connected to the battery assembly.

As used herein, the term vapor includes an aerosol and other fluid streams for provision to a user by the electronic vapor provision device.

BRIEF DESCRIPTION OF THE DRAWINGS

For a better understanding of the disclosure, and to show how example embodiments may be carried into effect, reference will now be made to the accompanying drawings in which.

DETAILED DESCRIPTION

Figure 1:
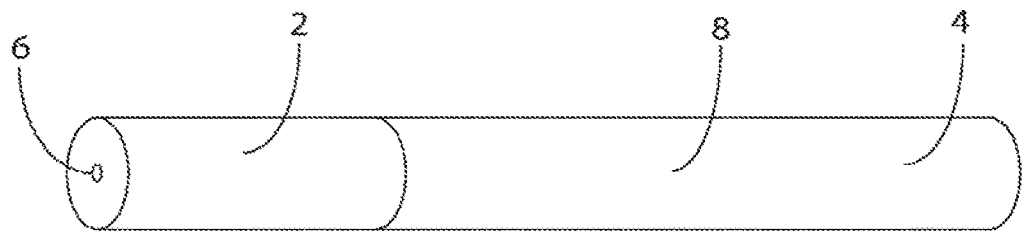
FIG. 1 is a side perspective view of an electronic vapor provision device.
Figure 2:
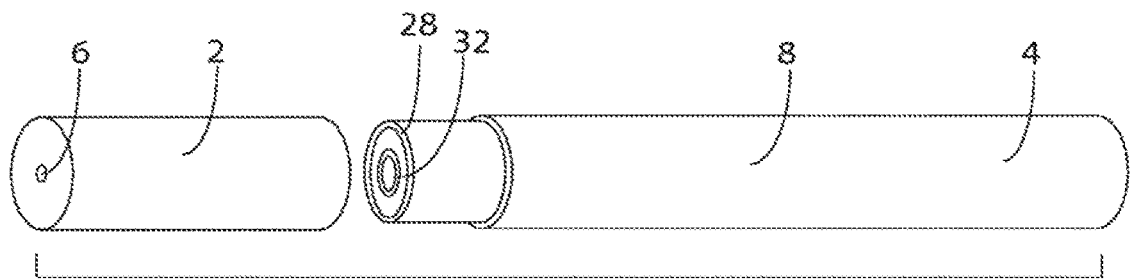
FIG. 2 is an exploded side perspective view of the electronic vapor provision device of FIG. 1.
Figure 3:
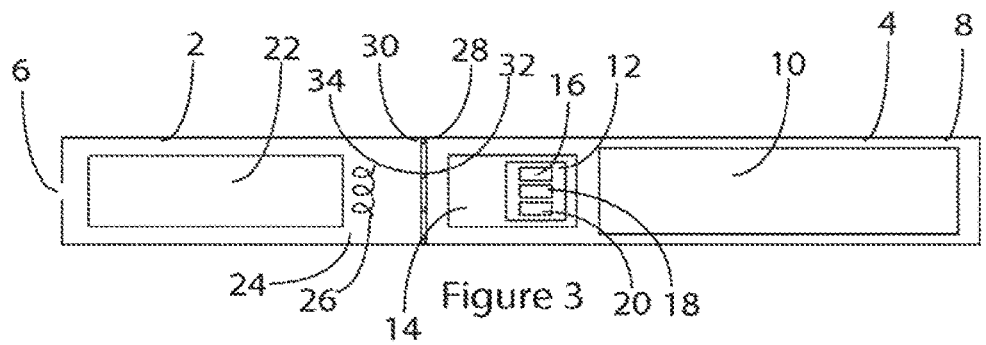
FIG. 3 is a side sectional view through the device of FIG. 1.

Referring to FIGS. 1 to 3, there is shown an electronic vapor provision device also referred to herein as an electronic smoking device, comprising a mouthpiece 2 and a body 4. The electronic vapor provision device is shaped like a conventional cigarette. Both the mouthpiece 2 and body 4 are cylindrical and are configured to connect to each other coaxially so as to form the conventional cigarette shape. The mouthpiece 2 is connectable to the body 4 at a first end of the mouthpiece and has an air outlet 6 at a second end. The body 2 comprises a battery assembly 8, comprising a power cell 10 and a computer 12 on a circuit board 14, wherein the power cell 10 is connected to the computer 12. The computer 12 comprises a computer processor 16, a memory 18 and input-output arrangement 20. In this example the computer 12 is a microcontroller. The computer 12 is configured to control and interface with the other electrical components of the battery assembly 8, comprising the power cell 10, via the input-output arrangement 20.

The mouthpiece 2 comprises a liquid bottle 22 and a vaporizer 24 having a heater coil 26. For example, the vaporizer 24 is in fluid communication with the liquid bottle 22. The mouthpiece 2 is connectable to the battery assembly 8 by a screw thread, wherein connection of the battery assembly 8 and the mouthpiece 2 connects a first battery assembly terminal 28 to a first vaporizer terminal 30 and a second battery assembly terminal 32 to a second vaporizer terminal 34, forming an electrically conductive contact in both cases. The vaporizer terminals 30 34 are electrically connected in parallel to the vaporizer 24.

The herein described configuration of the computer 12 comprises the computer operating according to a computer program stored in its memory 18 and accessed by its computer processor 16.

To maximize the lifetime of the charge in the power cell 10, the computer 12 is configured to detect whether the vaporizer 24 is connected to the battery assembly 8, the connection state, and to enter a low power sleep mode if the vaporizer 24 is not connected. For example, sleep mode may comprise the computer 12 consuming minimal power and performing no processing. A period during which the computer 12 is in sleep mode is herein referred to as sleep time. Furthermore, if the computer 12 determines that the vaporizer 24 is connected, the computer 12 is configured to enter a connected mode, which is of a higher power than the low power mode.

Moreover, detecting the connection state may comprise the computer 12 periodically checking whether the vaporizer 24 is connected to the battery assembly 8. If the computer 12 determines that the vaporizer 24 is not attached, the computer 12 goes into sleep mode for two seconds. After the sleep time, the computer 12 wakes and immediately and quickly checks again for a vaporizer connection. Again, if the vaporizer is not connected the computer 12 goes into sleep mode for another two seconds. The time that the computer 12 is awake is extremely short compared to the sleep time so the circuit remains predominantly in a low power mode, thus conserving power. During the sleep time no checks are made to determine whether the vaporizer 24 is connected. A user may take several seconds to assemble the device, connecting the vaporizer 24 and the battery assembly 8, so the vaporizer 24 connection may be easily established by the computer 12 before use of the device by a user.

The waking of the computer 12 may for example comprise the computer 12 entering a waking mode distinct from the sleep mode and the connection mode.

The computer 12 checking whether the vaporizer 24 is connected to the battery assembly 8 may for example comprise the computer 12 sending an electrical pulse to the battery assembly terminals 28, 32. For example, the computer 12 may control the power cell 10 so as to supply a pulse of current to the first battery assembly terminal 28 and may measure the current reaching the second the battery assembly terminal 32, for example using a digital multimeter of the battery assembly 8. The digital multimeter is referenced 44 in the circuit diagram of FIG. 10. Furthermore, if the vaporizer 24 is connected, the digital multimeter reads a current reaching the second battery assembly terminal 32 via the vaporizer 24 and provides information to the computer 12 indicating this.

Figure 4:
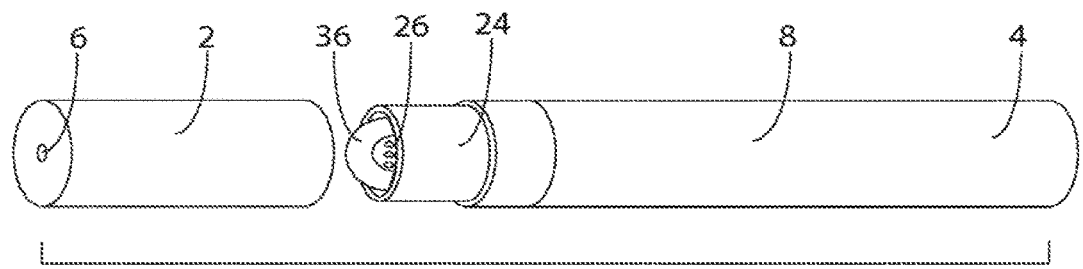
FIG. 4 is a side perspective view of an electronic vapor provision device with separated mouthpiece and body.
Figure 5:
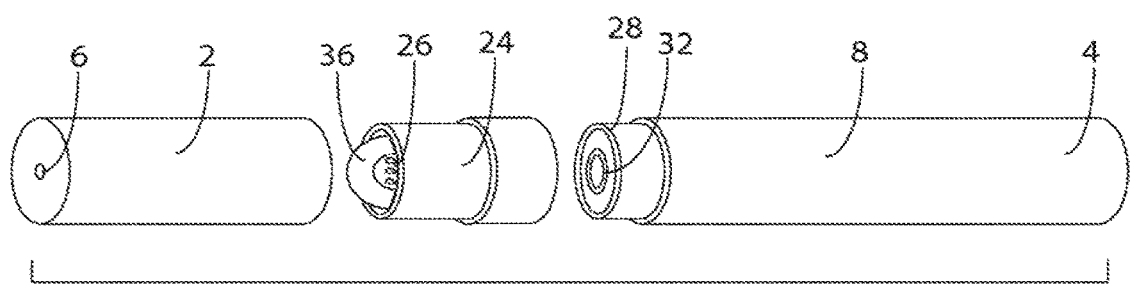
FIG. 5 is a side perspective view of an electronic vapor provision device with separated mouthpiece, vaporizer and battery assembly.
Figure 6:
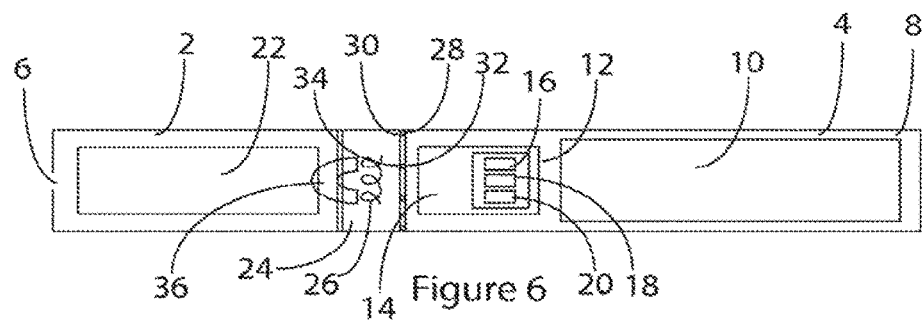
FIG. 6 is a side sectional view through the electronic vapor provision device of FIG. 4 with connected mouthpiece and body.

FIGS. 4 to 6 show another example of an electronic vapor provision device. This device is similar to that shown in FIGS. 1 to 3, however in this example the vaporizer 24 does not form part of the mouthpiece 2. The mouthpiece 2 contains a liquid bottle 22 and is attachable to the vaporizer 24. The vaporizer 24 has a heater coil 26 and additionally a wick 36. For example the wick 36 may be a mesh wick. The mouthpiece 2 and the vaporizer 24 are configured to connect to each other such that the wick 36 acts to communicate liquid from the liquid container 22 onto the vaporizer 24. The interaction between the vaporizer 24 and the battery assembly 8 to conserve power is as described above.

Further examples of how, in the devices of FIGS. 1 to 6, connection of the vaporizer 24 to the body 4 may be detected by the computer 12 are now described with reference to FIGS. 7 to 10.

Figure 7:
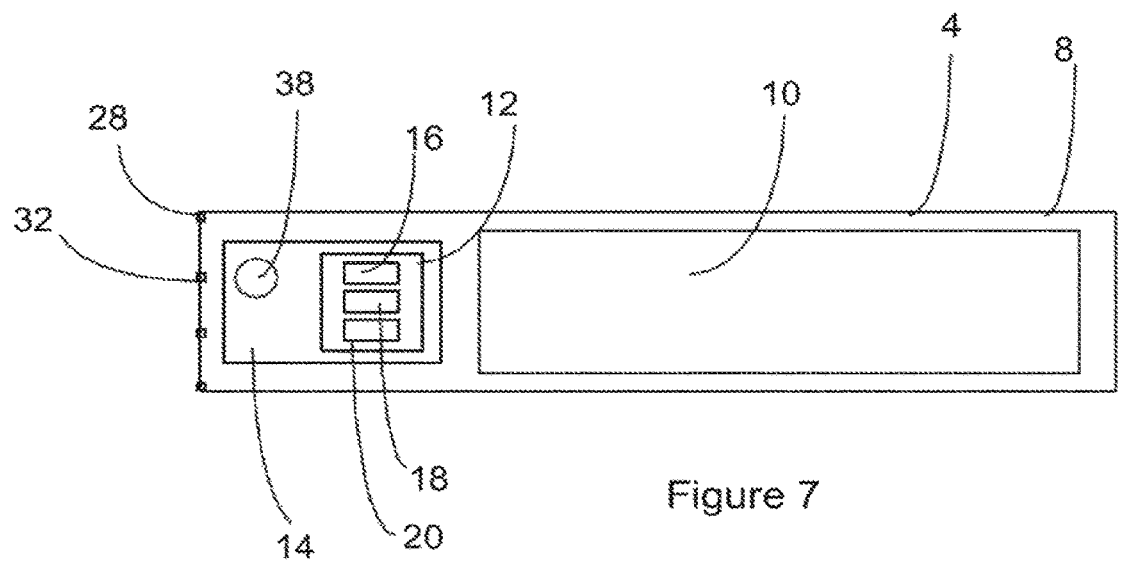
FIG. 7 is a side sectional view of a battery assembly having a capacitor.
Figure 8:
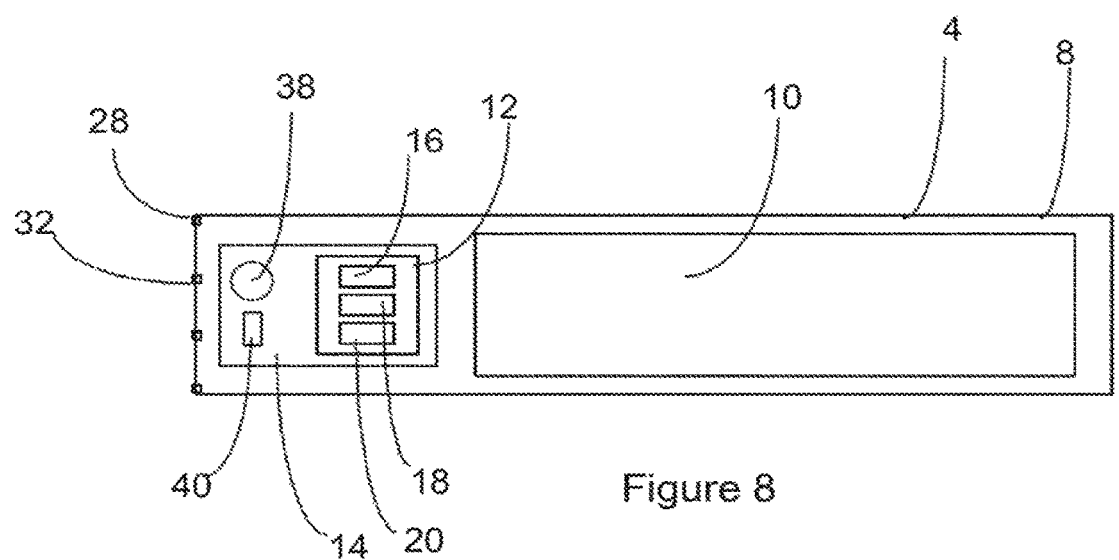
FIG. 8 is a side sectional view of a battery assembly having a capacitor and resistor.

FIG. 7 shows a battery assembly 8 similar to that shown in FIG. 3 and FIG. 6, additionally comprising a capacitor 38. The capacitor 38 is arranged in a circuit such that it is in parallel to the battery assembly terminals and to the power cell 10. To test whether the vaporizer 24 is connected to the battery assembly 8, the computer 12 first controls the power cell 10 to charge the capacitor 38, then waits a short time and checks the charge of the capacitor 38. For example, the computer 12 may use a digital multimeter of the battery assembly 8, wired in a switched parallel circuit to the capacitor 38, to check the charge of the capacitor 38. For instance, in order to check the charge of the capacitor 38, the computer 12 may trigger the completion of the switched digital multimeter circuit and may then receive information from the multimeter indicating a voltage across the capacitor 38 resulting from the charge of the capacitor. If the vaporizer 24 is connected, the resistance of the vaporizer 24 causes the capacitor 38 to discharge quickly so the computer 12 measures at least a substantially fully discharged capacitor 38. If the vaporizer 24 is not connected the capacitor is not substantially fully discharged when checked by the computer 12. FIG. 8 shows an arrangement similar to that shown in FIG. 7, additionally comprising a resistor 40 in series with the capacitor 38. For example, the resistor 40 and the capacitor 38 may be connected in series with each other and in parallel with the first and second battery assembly connection terminals 28 32.

The battery assembly 8 of the devices described herein may further comprise an air pressure sensor, wherein the air pressure sensor is powered by the power cell 10 and controlled by the computer 12. Once the vaporizer is connected to the battery assembly 8, and the device enters a connected mode after the computer 12 has determined the device's connection state, in order to use the device the user must suck on the mouthpiece 2. The electronic vapor provision device is configured such that the user sucking on the mouthpiece 2 causes a drop in air pressure at the air pressure sensor. The computer 12 therefore receives information from the air pressure sensor indicating that a user is sucking on the device. In response to this information, the computer 12 controls the power cell 10 to power the vaporizer 24. For example, the computer may control the power cell 10 to power the vaporizer 24 via the respective first and second terminals of both the battery assembly and the vaporizer. This causes the vaporization of liquid communicated to the vaporizer 24 from the liquid bottle 22. The provided vapor then passes to the user. Consequently, use of the device by a user comprises the user sucking on the device and the detection of this user interaction by the device so as to trigger the vaporization of the liquid contained in the device. The pressure sensor is referenced 43 in the circuit of FIG. 10 described in more detail hereinafter.

It should be noted that the herein described configuration of the computer 12 to determine whether the vaporizer 24 is connected to the battery assembly 8 does not require use of the device by the user.

Figure 9:
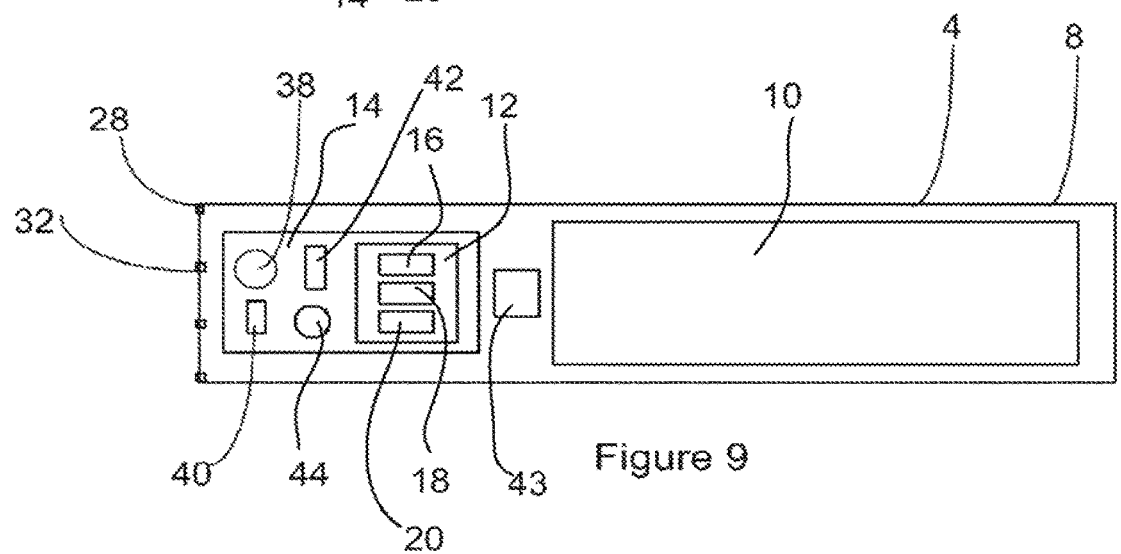
FIG. 9 is a side sectional view of a battery assembly having a capacitor, resistor and transistor.
Figure 10:
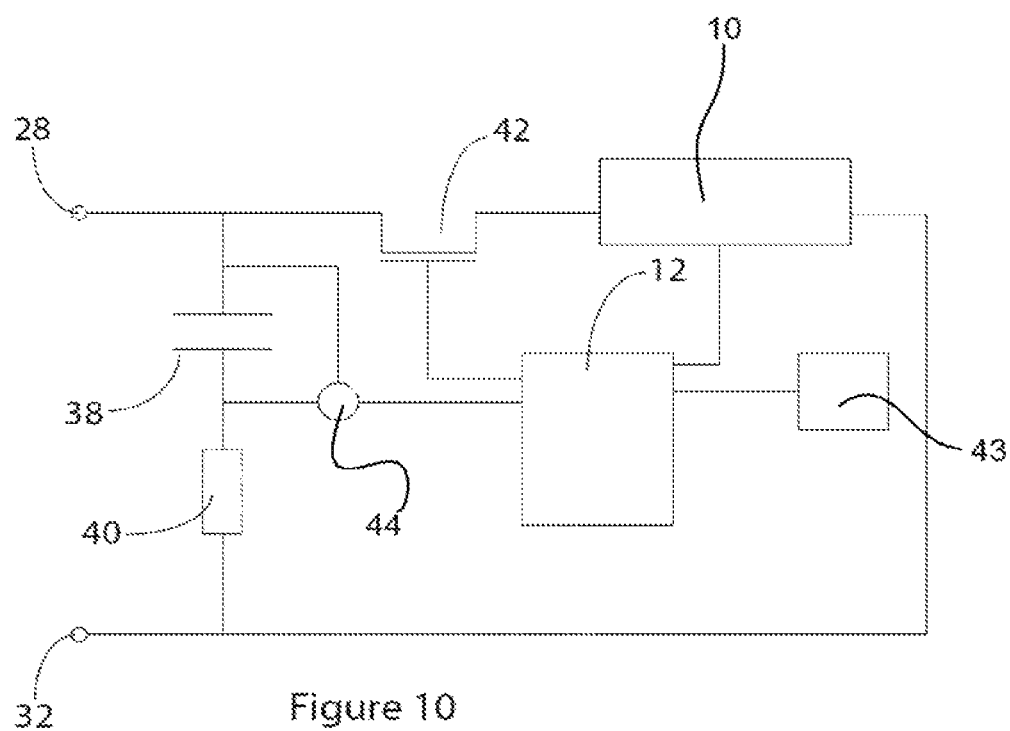
FIG. 10 is a circuit diagram for the battery assembly of FIG. 9.

FIG. 9 shows a battery assembly 8, comprising a digital multimeter 44, similar to that described with reference to FIGS. 7 and 8, further comprising a transistor 42 and the previously described air pressure sensor 43. FIG. 10 shows a circuit diagram of the battery assembly of FIG. 9.

The transistor 42 is connected in series between the power cell 10 and the capacitor 38.

In the example shown in FIG. 9 and FIG. 10, the previously described controlling of the charging of the capacitor 38 by the computer 12 involves the transistor 42. To test whether the vaporizer 24 is connected, the computer 12 sends a square wave pulse to the transistor 42. The transistor 42 supplies current to the capacitor 38 for a period of time equal to the width of the pulse, thereby charging the capacitor 38. For example the transistor 42 may be configured such that it opens a current from the power cell 10 to the capacitor 38 for a period of time equal to the width of the pulse. As described above, if the vaporizer 24 is connected the computer 12 measures at least a substantially fully discharged capacitor 38.

With regard to the embodiments described herein, the following alternatives and variations will now be described.

The electronic vapor provision devices described may be electronic cigarettes.

The sleep time may be substantially 2 seconds. However, the sleep time is not restricted to 2 seconds and other suitable values could be used. Moreover, the time between entering sleep modes can be significantly less than the sleep time.

The computer processor 16 can be a microprocessor. Moreover, the computer 12 may comprise a microcontroller. Furthermore, a computer such as a microcontroller could utilize a watchdog timer to implement the sleep time wait in the low power mode. Using a microcontroller has space saving advantages since the entire computer is located on a single chip and therefore the size of the device is minimized. Fewer components to assemble also provides reduced manufacturing times are costs. The computer is not restricted to being a microcontroller and could be fabricated from separate processor, memory and input-output components.

The device is not restricted to being cigarette shaped.

The vaporizer 24 and the battery assembly 8 may be releasably connectable to each other.

The vaporizers 24 described are examples only.

Moreover, the sleep mode may be the lowest non-zero power mode of the device. Although an air pressure sensor 43 is described, other configurations may be employed to detect when a user is attempting to use the device. For example, an airflow sensor may be used and the device may be configured such that sucking on the mouthpiece 2 by a user causes a flow of air past the air flow sensor.

Although a liquid bottle 22 is described, other types of liquid storage may be used. For example the device may comprise foam partially saturated in liquid for vaporization.

Although a digital multimeter 44 is described as being used by the computer 12 to determine the level of charge of the capacitor, other suitable configurations may be employed for this purpose. For example, a digital voltmeter may instead be used.

The pulse provided by the computer may be a square wave pulse.

Although examples have been shown and described it will be appreciated by those skilled in the art that various changes and modifications might be made without departing from the scope of the invention.

In order to address various issues and advance the art, the entirety of this disclosure shows by way of illustration various embodiments in which the claimed invention(s) may be practiced and provide for superior electronic vapor provision devices. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic vapor provision device comprising:
    a battery assembly and a vaporizer, wherein:
        the battery assembly comprises a power cell and a computer, the vaporizer is releasably-attachable to the battery assembly, the computer comprises a computer processor, a memory and an input-output means, the computer is configured in use to detect whether the vaporizer is connected to the battery assembly, the vaporizer comprises a liquid store, an electrical heater, and a mouthpiece, and the computer is configured to control a supply of power from the power cell to the electrical heater to vaporize liquid from the liquid store from inhalation by a user through the mouthpiece, the device is configured to substantially remain in a sleep mode until the vaporizer is connected to the battery assembly, wherein the sleep mode is a low power mode, the computer is configured to enter a connected mode when the vaporizer is connected to the battery assembly, the connected mode is a higher power state than the lower power mode to enable a more rapid activation once the device is activated by a user; and the battery assembly further comprises a capacitor, wherein the computer is configured to first charge the capacitor and then determine that the vaporizer is not connected to the battery assembly when the capacitor is not substantially fully discharged, and to determine that the vaporizer is connected to the battery assembly when the capacitor is substantially fully discharged.

2. The electronic vapor provision device of claim 1, wherein the computer is configured to wake from the sleep mode after a predetermined sleep time to determine whether the vaporizer is connected to the battery assembly, wherein the computer is configured to re-enter the sleep mode if the vaporizer is not connected to the battery assembly.

3. The electronic vapor provision device of claim 1, wherein the computer consumes minimal power and performs no processing in the sleep mode.

4. The electronic vapor provision device of claim 1, wherein the computer is configured to control and interface with other electrical components of the battery assembly via the input-output means.

5. The electronic vapor provision device of claim 1, wherein a computer program for controlling operations of the computer is stored in the memory for access by the computer processor.

6. The electronic vapor provision device of claim 1, wherein the computer is located on a circuit board.

7. The electronic vapor provision device of claim 1, wherein the device further comprises battery terminals for electrically connecting the battery assembly to the vaporizer, and the computer is configured to check whether the vaporizer is connected to the battery assembly by sending an electrical pulse to the battery terminals.

8. The electronic vapor provision device of claim 7, wherein the checking comprises the computer controlling the power cell to supply a pulse of current to a first battery terminal and measuring a current reaching a second battery terminal.

9. The electronic vapor provision device of claim 1, further comprising a sensor for detecting an inhalation on the device when the vaporizer is connected to the battery assembly, wherein the computer controls the power cell to supply power to the vaporizer in response to detecting an inhalation.

10. The electronic vapor provision device of claim 1, wherein the computer determining whether the vaporizer is connected to the battery assembly does not require use of the device by a user.

11. The electronic vapor provision device of claim 1, wherein the computer is a microcontroller.

12. The electronic vapor provision device of claim 1, wherein the computer is a microprocessor.

13. The electronic vapor provision device of claim 1, wherein the computer is provided on a single chip.

* * * * *